United States Patent [19]

Kleiner et al.

[11] Patent Number: 5,767,317

[45] Date of Patent: Jun. 16, 1998

[54] PROCESS FOR PREPARING 2,2'-BIS (DIPHENYLPHOSPHINYLMETHYL)-1,1'-BINAPHTHYLS AND NEW COMPOUNDS FROM THIS CLASS OF SUBSTANCES

[75] Inventors: Hans-Jerg Kleiner, Kronberg; Dieter Regnat, Eppstein; Horst Röschert, Ober-Hilbersheim, all of Germany

[73] Assignee: Hoechst Aktiengesellschaft, Frankfort, Germany

[21] Appl. No.: 826,017

[22] Filed: Mar. 27, 1997

Related U.S. Application Data

[63] Continuation of Ser. No. 408,063, Mar. 21, 1995, abandoned.

[30] Foreign Application Priority Data

Mar. 23, 1994 [DE] Germany .......................... 44 09 973.8
Sep. 19, 1994 [DE] Germany .......................... 44 33 295.5

[51] Int. Cl.[6] .................................................. C07F 9/50
[52] U.S. Cl. ................................................ 568/14; 568/17
[58] Field of Search ..................................... 568/14, 17

[56] References Cited

FOREIGN PATENT DOCUMENTS 2109470  4/1994  Canada.
0 595 150  10/1993  European Pat. Off..

OTHER PUBLICATIONS

Chemical Abstract, No. 91764v, vol. 91, 1979.

Tamao, et al., "Optimally Active 2,2'-Bis(Diphenylphosphinomethyl)-1,1'Binaphthyl: ...". Tetrahedron Letters No. 16 pp. 1389–1392, 1977.

European Search Report No. 95103403.2, Jun. 20, 1995.

Tetrahedron Lett. pp. 1889–92. Kyoto Univ. Dep. Synth. Chem. Kyoto, Japan.

Primary Examiner—Margaret W. Glass
Attorney, Agent, or Firm—Connolly & Hutz

[57] ABSTRACT

The present invention relates to a process for preparing 2,2'-bis(diphenylphosphinylmethyl)-1,1'-binaphthyls by reacting a reaction mixture prepared in a solvent by reaction of 2,2'-dimethyl-1,1'-binaphthyl with a brominating agent to produce a mixture comprising 2,2'-bis(bromomethyl)-1,1'-binaphthyl and further brominated binaphthyls and optionally further comprising unreacted brominating agent, reacted brominating agent and solvent, with an alkyl diphenylphosphinite of the formula $RO-P(Ph-(R')_n)_2$, where R is an alkyl radical having from 1 to 5 carbon atoms, Ph is phenyl, R' is an alkyl radical having from 1 to 4 carbon atoms, $CF_3$, fluorine, chlorine or bromine and n is 0, 1 or 2, at from 70° to 180° C. optionally in the presence of a further solvent.

31 Claims, No Drawings

PROCESS FOR PREPARING 2,2'-BIS (DIPHENYLPHOSPHINYLMETHYL)-1,1'-BINAPHTHYLS AND NEW COMPOUNDS FROM THIS CLASS OF SUBSTANCES

This application is a continuation of U.S. Ser. No. 08/408,063, filed Mar. 21, 1995, now abandoned.

The present invention relates to an improved process for preparing 2,2'-bis(diphenylphosphinylmethyl)-1,1'-binaphthyls and also new compounds from this class of substances.

2,2'-Bis(diphenylphosphinylmethyl)-1,1'-binaphthyl (formula I) is an important precursor for the preparation of 2,2'-bis(diphenylphosphinomethyl)-1,1'-binaphthyl (formula II), a bidentate phosphine (phosphane) which is used as a ligand for catalysts, for example in the coupling of haloaromatics catalyzed by metal complexes.

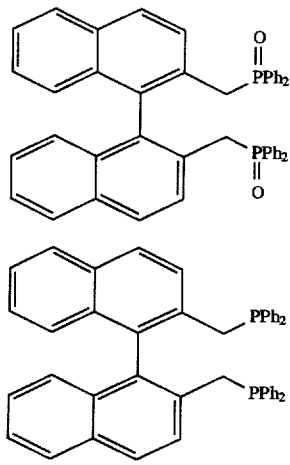

2,2'-Bis (diphenylphosphinylmethyl)-1,1'-binaphthyl can be prepared in the following manner. The starting material is the corresponding aromatic methyl compound, namely 2,2'-dimethyl-1,1'-binaphthyl, and the methyl group is brominated using N-bromosuccinimide to give 2,2'-bis-(bromomethyl)-1,1'-binaphthyl (formula III). In this reaction, which is described a number of times in the literature and is carried out in the presence of a free-radical former but without the action of light, tetra-chloromethane is generally used as solvent (M. E. Jung et al., Tetrahedron Lett. 29 (1988) 6199; H. J. Bestmann et al., Chem. Ber. 107 (1974) 2926; J.-P. Mazaleyrat, Chem. Commun. 1985, 317; T. Hayashi et al., J. Am. Chem. Soc. 110 (1988) 8153).

Owing to the comparatively low boiling point of tetrachloromethane, namely 76.5° C., a reaction at higher temperatures can only be carried out under pressure, which requires additional technical complication. Furthermore, the yield of 2,2'-bis(bromomethyl)-1,1'-binaphthyl achievable by this process is, at about 60%, not very high.

The bromination of 2,2'-dimethyl-1,1'-binaphthyl gives, besides the desired product (formula III) essentially two byproducts, presumably 2-bromomethyl-2'-methyl-1,1'-binaphthyl and 2-dibromomethyl-2'-bromomethyl-1,1'-binaphthyl.

Although the isolation of 2,2'-bis(bromomethyl)-1,1'-binaphthyl in pure form can be successfully carried out by crystallization or by column chromatography, this is at the cost of, on the one hand, considerable yield losses or, in the case of column chromatography, very high technical complication.

The unpublished European Patent Application EP 93 116 788.6, which goes back, inter alia, to the unpublished German Patent Application P 43 08 562.8, describes the preparation of 2,2'-bis(bromomethyl)-1,1'-binaphthyl by reaction of 2,2'-dimethyl-1,1'-binaphthyl with N-bromosuccinimide in the presence of benzoyl peroxide, but without the action of light, in chlorobenzene. After the reaction is complete, the solvent is evaporated, the residue is taken up in ethyl acetate and washed first with 10% strength $Na_2SO_3$ solution then with saturated $Na_2CO_3$ solution and finally with saturated NaCl solution. After drying and recrystallization, this gives a yield of 65%. However, this process proves to be complicated (evaporation of the solvent, transfer of the residue into another solvent and washing three times with an aqueous sodium salt solution each time), in addition the yield also leaves something to be desired.

The bromination of 2,2'-dimethyl-1,1'-binaphthyl generally leads to a product mixture which is problematical to handle. It has thus been found that the removal of the solvent, even when carried out under gentle conditions (vacuum), leads to a mixture which is thermally unstable and begins to decompose exothermically above a temperature of only 50° C.

It is known from Houben-Weyl, Methoden der organischen Chemie, volume V/4, pages 333 and 334, that aralkyl bromides in the pure state are colorless substances usually having little thermal stability and some of them cannot be distilled without decomposition, even in vacuo. Naphthylmethyl bromides are generally less stable then benzyl bromides.

For this reason, the isolation of the crude product formed in the bromination is encumbered by a considerable hazard potential which, in particular for the large amounts of starting materials or raw materials handled on an industrial scale, poses an unpredictable risk.

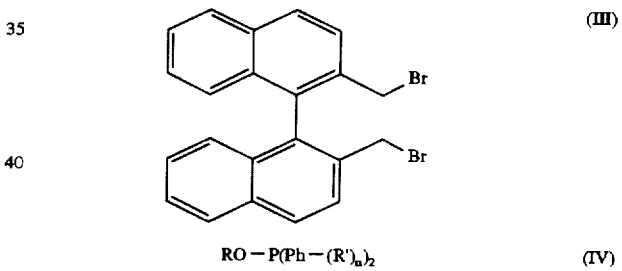

To prepare 2,2'-bis(diphenylphosphinylmethyl)-1,1'-binaphthyl (formula I), pure 2,2'-bis(bromomethyl)-1,1'-binaphthyl, i.e. not a mixture of various brominated binaphthyls, can be subjected to the Arbusov reaction with methyl diphenylphosphinite (formula IV, where R is $CH_3$ and n is 0) without addition of a solvent. As described in JP 7 939 059 or Chemical Abstract 91,91764 v, the two abovementioned components are heated in a ratio of 1:6.7 for three hours at 130° C. to give the desired product (formula I). The reaction is, however, problematical, since, as can be seen from Experiment 4 of JP 7 939 059, an explosive reaction occurs at 87° C. The yield achieved is only 30%. The process is not suitable for an industrial process, neither with regard to the required process safety nor with regard to the yield.

There is therefore a need to develop a process for preparing 2,2'-bis(diphenylphosphinylmethyl)-1,1'-binaphthyls which does not have the abovementioned disadvantages, can also be carried out simply and reliably and enables the desired product to be obtained in high yield and purity.

This object is achieved by a process for preparing 2,2'-bis(diphenylphosphinylmethyl)-1,1'-binaphthyls. It comprises reacting a reaction mixture prepared in a solvent by reaction of 2,2'-dimethyl-1,1'-binaphthyl with a brominating agent and containing 2,2'-bis(bromomethyl)-1,1'-binaphthyl and further brominated binaphthyls, if desired after removal of unreacted brominating agent, reacted brominating agent and/or solvent, with an alkyl diphenylphosphinite of the formula (IV) RO—P(Ph—(R')$_n$)$_2$, where R is an alkyl radical having from 1 to 5, in . particular from 1 to 3, carbon atoms, Ph is phenyl, R' is an alkyl radical having from 1 to 4 carbon atoms, CF$_3$, fluorine, chlorine or bromine, in particular methyl, CF$_3$ or fluorine, and n is 0, 1 or 2, at from 70 to 180° C. in the presence or absence of a further solvent.

An advantage of the process of the invention is that in the preparation of the reaction mixture, isolation of the 2,2'-bis (bromomethyl)-1,1'-binaphthyl (formula III) is omitted and in this way a quite complicated separation operation, which owing to the thermal instability of the reaction product formed in the bromination also presents a safety risk, is avoided. Furthermore, with suitable selection of the solvent, the solvent used in the reaction can remain in the reaction mixture. It does not have to be removed from the reaction mixture.

However, it is also possible to replace, if required, the solvent originally used in the bromination step by a further solvent and to completely or partially distil off the solvent originally used. In this way, although the solvent originally used is replaced by the further solvent, a quite complicated separation operation (isolation of the 2,2'-bis(bromomethyl) -1,1'-binaphthyl) can nevertheless be avoided.

The reaction mixture contains, independently of the method of bromination, the brominated compounds usually formed in a bromination, namely, besides the desired product, essentially presumably the two abovementioned brominated byproducts and also the solvent. The reaction mixture generally obtained contains from 60 to 85 mol %, in particular from 65 to 83 mol %, of 2,2'-bis(bromomethyl)-1,1'-binaphthyl and from 40 to 15 mol %, in particular from 35 to 17 mol %, of further brominated binaphthyls, with the solvent still present not being taken into account.

The one byproduct, presumably 2-bromomethyl-2'-methyl-1,1'-binaphthyl, makes up from 1 to 20 mol %, in particular from 3 to 18 mol %, and the other byproduct, presumably2-dibromomethyl-2'-bromomethyl-1,1'-binaphthyl makes up from 3 to 20 mol %, in particular from 5 to 17 mol %. The method of bromination also influences to a certain extent both the amount of the brominated binaphthyls formed and also the ratio in which the two abovementioned byproducts are formed.

In general, the amount of solvent used is of no great importance. However, a sufficient amount should be used. In general it is sufficient to use 2,2'-dimethyl-1,1'-binapthyl and the solvent in a weight ratio of 1:(3 to 40), in particular 1:(4 to 20), preferably 1:(5 to 15).

Solvents which can be used are generally those which are inert under the reaction conditions of the bromination.

Use can be made of monochlorinated or polychlorinated benzene, a monochlorinated or polychlorinated aliphatic hydrocarbon, an ester of an aliphatic carboxylic acid having from 1 to 6 carbon atoms and an alkyl alcohol having from 1 to 4 carbon atoms or mixtures thereof as solvents. Examples of such solvents are chloroform, dichloromethane, tetrachloromethane, chlorobenzene, ortho-, meta- and para-dichlorobenzene, methyl formate, ethyl formate, methyl acetate, ethyl acetate, propyl acetate, methyl propionate, ethyl propionate and propyl propionate. Well-suited solvents are chlorobenzene or dichlorobenzene or any mixture of these solvents. Chloro-benzene is particularly useful.

In some cases, esters of the abovementioned type, in particular methyl and ethyl esters of aliphatic carboxylic acids having from 1 to 3 carbon atoms, can also be used with good results.

In the preparation of the reaction mixture, the bromination can be carried out under the action of light having a wavelength of from $10^{-5}$ to $10^{-8}$ m, in particular from $10^{-6}$ to $2 \times 10^{-7}$. It is here usual to allow the reaction of 2,2'-dimethyl-1,1'-binaphthyl to proceed at from −10 to 75° C. In many cases, it is found to be sufficient to react 2,2'-dimethyl-1,1'-binaphthyl with the brominating agent at from −5° to 50° C., in particular from 0° to 40° C. The light source used for the bromination can be a conventional UV irradiator, for example a daylight lamp, a doped or undoped mercury vapor lamp or low-pressure mercury vapor lamp. On the other hand, 2,2'-dimethyl-1,1'-binaphthyl and the brominating agent can be reacted in the absence of light, but in the presence of a free-radical former at from 25° to 150° C., in particular from 40° to 135° C.

The bromination can be carried out using a customary brominating agent, for example bromine, N-bromosuccinimide, 1,3-dibromo-5,5-dimethylhydantoin, brominated Meldrum's acid.

It has been found to be favorable to react 2,2'-dimethyl-1,1'-binaphthyl with N-bromosuccinimide as brominating agent. 2,2'-Dimethyl-1,1'-binaphthyl and N-bromosuccinimide are usually used in a molar ratio of 1:(1.5 to 2.5), in particular 1:(1.8 to 2.3), preferably 1:(1.9 to 2.2).

In the course of the bromination, N-bromosuccinimide forms succinimide which, if desired after cooling the solution containing the reaction product, is removed by filtration. A further possibility is to remove the succinimide formed by extraction with water. For this purpose, from 10 to 100% by weight of water, based on reaction mixture, are usually used.

A particularly simple and at the same time effective method of removing succinimide is to separate the succinimide formed from the reaction mixture in a first step by filtration and in a second step by extraction with water. This uses comparatively little water and accordingly also gives little wastewater.

The bromination carried out under the action of light gives the desired product in a yield of about 80%. In addition, it usually gives from 1 to 6% of a brominated substance, presumably 2-bromomethyl-2'-methyl-1,1'-binaphthyl, and from 7 to 13% of a further byproduct, presumably 2-dibromomethyl-2'-bromomethyl-1,1'-binaphthyl.

The corresponding reaction mixture (A) used in the Arbusov reaction presumably contains, besides small amounts of substances not identified in more detail, the abovementioned bromo compounds dissolved in the solvent, for example in chlorobenzene and/or dichlorobenzene, in particular in chlorobenzene.

In place of the reaction mixture (A) prepared under the action of light, it is also possible to use a reaction mixture (B) which can be obtained, for example, by reaction of 2,2'-dimethyl-1,1'-binaphthyl with N-bromo-succinimide in the presence of a solvent under the action of a free-radical former (free-radical initiator) and by subsequent removal of succinimide, with good results in the Arbusov reaction (reaction with the alkyl diphenyl-phosphinite). Such a reaction mixture (B) can be prepared by reacting 2,2'-dimethyl-1,1'-binaphthyl with N-bromo-succinimide, for example in a molar ratio of 1:(1.5 to 2.5), in particular 1:(1.8 to 2.3), preferably 1:(1.9 to 2.2), at elevated temperature, usually at temperatures of from 25° to 150° C., in particular from 40° to 135° C., under the action of a free-radical initiator in chlorobenzene and/or dichlorobenzene, removing succinimide formed, but without removing the chlorobenzene and/or dichlorobenzene used as solvent.

Suitable free-radical initiators are the customary free-radical formers, for example organic peroxides, hydroperoxides, azobisisobutyronitrile.

The bromination carried out under the action of the free-radical initiator gives the desired product in a yield of from about 63 to 67 %. In addition, it generally gives from 10 to 20 % of a brominated product, presumably 2-bromomethyl-2'-methyl-1,1'-binaphthyl, and from 8 to 15 % of a further byproduct, presumably 2-dibromomethyl-2-bromomethyl-1,1'-binaphthyl. The reaction mixture (B) used in the Arbusov reaction presumably contains, besides small amounts of substances not identified in more detail, the abovementioned bromo compounds dissolved in chlorobenzene and/or dichlorobenzene, in particular chlorobenzene.

The succinimide formed from the N-bromosuccinimide is separated from the bromination mixture, if desired after cooling, by filtration. Another possibility is to carry out the subsequent removal of succinimide by extraction with water.

A particularly simple and effective variant is to separate succinimide from the bromination mixture in a first step by filtration and in a second step by extraction with water.

Unreacted free-radical formers can be removed, for example, by scrubbing with an aqueous $Na_2SO_3$ solution.

The abovedescribed procedure gives the reaction mixture (B).

To carry out the Arbusov reaction, the reaction mixture, for example the reaction mixture (A) or the reaction mixture (B), is reacted with an alkyl diphenylphosphinite (formula IV), as already mentioned above, at from 70° to 180° C. In many cases, it is sufficient to carry out the reaction at from 100° to 170° C., in particular from 120° to 160° C. The reaction proceeds according to the following equation:

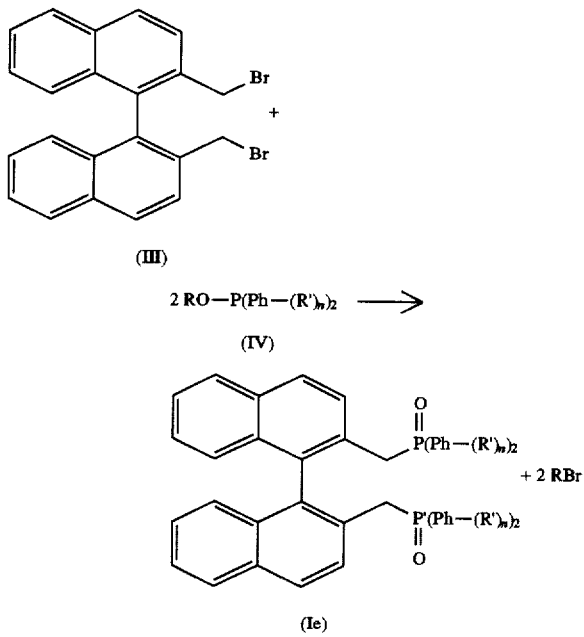

The alkyldiphenylphosphinite of the formula (IV) used is usually a $(C_1-C_5)$alkyl diphenylphosphinite or a mixture of these esters. Suitable alkyl diphenylphosphinites are, without claiming completeness, methyl diphenylphosphinite, ethyl diphenylphosphinite, isopropyl diphenylphosphinite, n-propyl diphenylphosphinite, ethyl bis(3-fluorophenyl) phosphinite, ethyl bis(4-fluorophenyl)-phosphinite, ethyl bis (2-methylphenyl)phosphinite and/or ethyl bis(3-trifluoromethylphenyl)phosphinite.

The alkyl diphenylphosphinite is generally used in a molar ratio of (1.8 to 4):1, in particular (1.9 to 3):1, preferably (2 to 2.5):1, based on the 2,2'-dimethyl-1,1'-binaphthyl. However, in many cases it is possible to use the alkyl diphenylphosphinite (formula IV), based on 2,2'-dimethyl-1,1'-binaphthyl used, in the stoichiometric ratio or in a slight excess.

Before the reaction mixture resulting from the bromination stage is used in the subsequent Arbusov reaction (reaction with the alkyl diphenylphosphinite), it is advisable, as mentioned above, in many cases to remove the unreacted brominating agent and/or the reacted brominating agent and/or the solvent used in the bromination stage.

Unreacted brominating agent, for example bromine, can be removed by vaporization, reacted brominating agent, for example succinimide, can be removed by filtration and extraction. The solvent used in the bromination stage is replaced by a further solvent which has a boiling point higher than that of the solvent originally used. The further solvent is added prior to the reaction or during the reaction or after the reaction of the reaction mixture with the alkyl diphenylphosphinite and the solvent originally used is subsequently distilled off. This removal of the original solvent can be carried out prior to the Arbusov reaction or even during the Arbusov reaction or after the Arbusov reaction. If a solvent which is inert to the Arbusov reaction is used as original solvent, it can be removed during the Arbusov reaction or the removal can even be omitted. Such solvents are, for example, chlorobenzene, dichlorobenzene and mixtures thereof; when they are used a removal is not absolutely necessary.

Solvents which are not inert to the Arbusov reaction have to be removed prior to carrying out the Arbusov reaction. Such solvents are, for example, monochlorinated or polychlorinated aliphatic hydrocarbons.

Suitable further solvents are generally solvents which have a boiling point higher than that of the solvent originally used and which are inert under the conditions of the Arbusov reaction. These include aromatic hydrocarbons, for example toluene, o-xylene, m-xylene, p-xylene, mixtures of these xylenes, ethylbenzene and/or mesitylene and high-boiling aliphatic hydrocarbons, for example petroleum ether having a boiling point >100° C., decalin, ligroin and/or isooctane.

The Arbusov reaction can thus be carried out in the presence or absence of a further solvent.

In some cases it has been found to be advantageous to add the further, nonpolar solvent which has a boiling point higher than that of the solvent originally used during the Arbusov reaction (reaction with the alkyl diphenylphosphinite) and to simultaneously distill off the solvent originally used, for example chlorobenzene and/or dichlorobenzene. Suitable solvents for this purpose are, for example, aromatic compounds having boiling points higher than chlorobenzene and/or dichlorobenzene, for example o-xylene, m-xylene, p-xylene, mixtures of these xylenes and/or mesitylene. This allows the yield of 2,2'-bis (diphenylphosphinylmethyl)-1,1'-binaphthyl isolated to be increased somewhat further.

It is surprising that the brominated binaphthyls, for example the brominated byproducts present in both the reaction mixture (A) and in the reaction mixture (B) generally do not interfere in the Arbusov reaction and also do not impair the quality of the desired final product (formula I).

Furthermore, it is unexpected that the use of a solvent, for example the use of chlorobenzene and/or dichlorobenzene, in the Arbusov reaction leads to a significant increase in yield. While the process of JP 7 939 059 gives a yield of only 30%, the process of the invention gives a yield of from 90 to 95% of desired product, in each case based on 2,2'-bis(bromomethyl)-1,1'-binaphthyl. In addition, the danger of the reaction occurring explosively is avoided.

To carry out the Arbusov reaction, the reaction mixture, for example reaction mixture (A) or the reaction (B) or mixtures of the two reaction mixtures, is usually initially charged and heated to the prescribed temperature. It is advantageous to select a temperature below the boiling point of the solvent used. After reaching the reaction temperature, the alkyl diphenyl-phosphinite is slowly added dropwise to the initially charged reaction solution. As the reaction proceeds, it results in the formation of alkyl bromide which is continuously distilled from the reaction product. If desired, the mixture can also be boiled under reflux for some time after the end of the addition of the alkyl diphenylphosphinite, so as to complete the reaction.

If it is intended that the solvent originally used be removed during the Arbusov reaction, a temperature above the boiling point of the original solvent but below that of the further solvent added is selected. In this way, both the alkyl bromide and also the solvent originally used distills off.

The process of the invention makes it possible to obtain the new compounds of the formula (Ia)

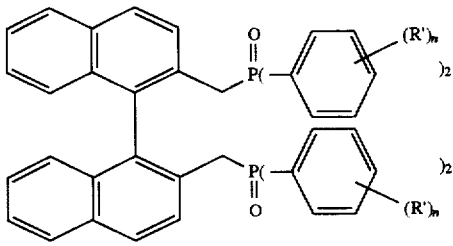

where R' is an alkyl radical having from 1 to 4 carbon atoms, $CF_3$, fluorine, chlorine or bromine, in particular methyl, $CF_3$ or fluorine, and n is 1 or 2, in a surprisingly simple manner by reaction of 2,2'-bis(bromo-methyl)-1,1'-binaphthyl of the formula (III) with the corresponding diphenylphosphinic ester of the formula IV.

New compounds in this category which may be mentioned are, in particular, 2,2'-bis[bis(3-fluorophenyl)phosphinylmethyl]-1,1'-binaphthyl, 2,2'-bis[bis(4-fluorophenyl)phosphinylmethyl]-1,1'-binaphthyl, 2,2'-bis[bis(2-methylphenyl)phosphinylmethyl]-1,1'-binaphthyl and 2,2'-bis [bis(3-trifluoromethylphenyl)phosphinylmethyl]-1,1'-binaphthyl.

The following examples illustrate the invention without limiting it.

Experimental part

EXAMPLE 1
Preparation using a reaction mixture A

With exclusion of moisture, 282.4 g (1.0 mol) of 2,2'-dimethyl-1,1'-binaphthyl and 373.8 g (2.1 mol) of N-bromosuccinimide are suspended in 1.7 l of chlorobenzene in a 4 l glass flask and are illuminated with a UV immersion lamp for 8 hours at from 5° to 10° C. The precipitated succinimide is filtered off, the solution is extracted twice with 200 ml of water each time, dried using sodium sulfate and filtered. The filtrate (reaction mixture A)* is transferred to a 4 l four-neck flask fitted with stirrer, dropping funnel, reflux condenser and internal thermometer and is heated to 125° C. 460.5 g (2.0 mol) of ethyl diphenylphosphinite are then slowly added dropwise, with ethyl bromide distilling off. After the end of the addition, the mixture is heated under reflux for a further two hours and is then cooled to 0° C. The solid is filtered off, washed with cold chlorobenzene and dried in vacuo. This gives 512 g (purity: >99 %) of 2,2'-bis(diphenylphosphinylmethyl)-1,1'-binaphthyl as colorless crystals having a melting point of from 287° to 289° C., corresponding to 75% total yield based on 2,2'-dimethyl-1,1'-binaphthyl used.

Composition according to GC analysis (in mol %) without solvent: 80% of 2,2'-bis(bromomethyl)-1,1'-binaphthyl 2% of 2-bromomethyl-2'-methyl-1,1'-binaphthyl 13% of 2-dibromomethyl-2'-bromomethyl-1,1'-binaphthyl.

EXAMPLE 2
Preparation using a reaction mixture A

With exclusion of moisture, 282.4 g (1.0 mol) of 2,2'-dimethyl-1,1'-binaphthyl and 373.8 g (2.1 mol) of N-bromosuccinimide are suspended in 1.7 l of chlorobenzene in a 4 l glass flask and are illuminated with a UV immersion lamp for 8 hours at from 5° to 10° C. The precipitated succinimide is filtered off, the solution is extracted twice with 200 ml of water each time, dried using sodium sulfate and filtered. The filtrate (reaction mixture A)* is transferred to a 4 l four-neck flask fitted with stirrer, dropping funnel, reflux condenser and internal thermometer and is heated to 125° C. 488.6 g (2.0 mol) of propyl diphenylphosphinite are then slowly added dropwise, with n-propyl bromide distilling off. After the end of the addition, the mixture is heated under reflux for a further two hours and is then cooled to 0° C. The solid is filtered off, washed with cold chlorobenzene and dried in vacuo. This gives 502.5 g of 2,2'-bis (diphenylphosphinylmethyl)-1,1'-binaphthyl (purity: >99 %) as colorless crystals having a melting point of from 287° to 289° C., corresponding to 73.5 % total yield based on 2,2'-dimethyl-1,1'-binaphthyl used.

Composition according to GC analysis (in mol %) without solvent: 68% of 2,2'-bis(bromomethyl)-1,1'-binaphthyl 15% of 2-bromomethyl-2'-methyl-1,1'-binaphthyl 13% of 2-dibromomethyl-2'-bromomethyl-1,1'-binaphthyl.

EXAMPLE 3
Preparation using a reaction mixture B

With exclusion of moisture, 282.4 g (1.0 mol) of 2,2'-dimethyl-1,1'-binaphthyl, 373.8 g (2.1 mol) of N-bromosuccinimide and 500 mg of benzoyl peroxide are suspended in 1.7 l of chlorobenzene in a 4 l glass flask and are stirred for 3.5 hours at the boiling point. The precipitated succinimide is filtered off, the solution is extracted twice with 200 ml of water each time and once with 100 ml of $Na_2SO_3$ solution, dried using sodium sulfate and filtered. The filtrate (reaction mixture B)* is transferred to a 4 l four-neck flask fitted with stirrer, dropping funnel, reflux condenser and internal thermometer and is heated to 125° C. 460.5 g (2.0 mol) of ethyl diphenylphosphinite are then slowly added dropwise, with ethyl bromide distilling off. After the end of the addition, the mixture is heated under reflux for a further two hours and is then cooled to 0° C. The solid is filtered off, washed with cold chlorobenzene and dried in vacuo. This gives 443.8 g (purity: >99 %) of 2,2'-bis-(diphenylphosphinylmethyl)-1,1'-binaphthyl as colorless crystals having a melting point of from 287° to 289° C., corresponding to 65% total yield based on 2,2'-dimethyl-1,1'-binaphthyl used.

Composition according to GC analysis (in mol %) without solvent: 68% of 2,2'-bis(bromomethyl)-1,1'-binaphthyl 15% of 2-bromomethyl-2'-methyl-1,1'-binaphthyl 13% of 2-dibromomethyl-2'-bromomethyl-1,1'-binaphthyl.

EXAMPLE 4
2,2'-Bis[bis(3-fluorophenyl)phosphinylmethyl]-1,1'-binaphthyl

While stirring under nitrogen, 8.8 g (33 mmol) of ethyl bis(3-fluorophenyl)phosphinite are slowly added dropwise to a solution of 7.27 g (16.6 mmol) of 2,2'-bis(bromomethyl)-1,1'-binaphthyl in 40 ml of o-xylene, which solution has been heated to 120° C., with ethyl bromide distilling off. After the end of the addition, the mixture is heated under reflux for a further two hours and is then cooled to 0° C. The solid is filtered off, washed with cold o-xylene and dried in vacuo. This gives 11.5 g (91 %) of colorless crystals having a melting point of 280°–284° C.

$^{31}$p-NMR: δ (CDCl$_3$)=27.3 ppm

EXAMPLE 5
2,2'-Bis[bis(4-fluorophenyl)phosphinylmethyl]-1,1'-binaphthyl

While stirring under nitrogen, 10.70 g (0.04 mol) of ethyl bis(4-fluorophenyl)phosphinite are added dropwise to a solution of 8.80 g (0.02 mol) of 2,2'-bis(bromo-methyl)-1,1'-binaphthyl in 40 ml of o-xylene, which solution has been heated to 135° C. After the end of the addition, the mixture is heated under reflux for a further 1.5 hours. After cooling to room temperature, the precipitated crystals are filtered off with suction and washed with xylene. This gives 14.1 g (94 %) of colorless crystals having a melting point of 211°–214° C.

$^{31}$P-NMR: δ (CDCl$_3$)=28.2 ppm

EXAMPLE 6
2,2'-Bis[bis(2-methylphenyl)phosphinylmethyl]-1,1'-binaphthyl

While stirring under nitrogen, 21.5 g (83 mmol) of ethyl bis(2-methylphenyl)phosphinite are slowly added dropwise to a solution of 18.4 g (42 mmol) of 2,2'-bis(bromo-methyl)-1,1'-binaphthyl in 100 ml of o-xylene, which solution has been heated to 120° C., with ethyl bromide distilling off. After the end of the addition, the mixture is heated under reflux for a further two hours and is then cooled to 0° C. The solid is filtered off, washed with cold o-xylene and dried in vacuo. This gives 25.1 g (81%) of colorless crystals having a melting point of 231°–234° C.

$^{31}$P-NMR: δ (CDCl$_3$)=30.5 ppm

EXAMPLE 7
2,2'-Bis[bis(3-trifluoromethylphenyl)phosphinylmethyl]-1,1'-binaphthyl While stirring under nitrogen, 20.1 g (55 mmol) of ethyl bis(3-trifluoromethylphenyl)phosphinite are slowly added dropwise to a solution of 11.0 g (25 mmol) of 2,2'-bis(bromomethyl)-1,1'-binaphthyl in 80 ml of o-xylene, which solution has been heated to 120° C., with ethyl bromide distilling off. After the end of the addition, the mixture is heated under reflux for a further two hours and is then cooled to 0° C. The solid is filtered off, washed with cold o-xylene and dried in vacuo. This gives 16.1 g (68 %) of colorless crystals.

$^{31}$P-NMR: δ (CDCl$_3$)=27.1 ppm

EXAMPLE 8
(Arbusov in ethyl acetate)

While stirring under nitrogen, 88.5 g (385 mmol) of ethyl diphenylphosphinite are slowly added dropwise to a solution of 77.0 g (175 mmol) of 2,2'-bis(bromomethyl)-1,1'-binaphthyl in 400 ml of ethyl acetate, which solution has been heated to 78° C., and ethyl bromide is simultaneously distilled off via an 80 cm Vigreux column. After the end of the addition, the mixture is heated under reflux for a further two hours and is then cooled to 0° C. The solid is filtered off, washed with cold ethyl acetate and dried in vacuo. This gives 85.0 g (71%) of colorless crystals having a melting point of 287°–289° C.

We claim:

1. A process for preparing 2,2'-bis(diphenylphosphinylmethyl)-1,1=-binaphthyls, which comprises reacting:
   (a) a reaction mixture prepared in an initial solvent by brominating 2,2'-dimethyl-1,1'-binaphthyl with a brominating agent, the reaction mixture containing 2,2'-bis(bromomethyl)-1,1'-binaphthyl and other brominated binaphthyls, and may further contain unreacted brominating agent, reacted brominating agent and initial solvent;
   with (b) an alkyl diphenylphosphinite of the formula RO—P(Ph—(R')$_n$)$_2$, where R is an alkyl radical having from 1 to 5 carbon atoms, Ph is phenyl, R' is an alkyl radical having from 1 to 4 carbon atoms, CF$_3$, fluorine, chlorine or bromine and n is 0, 1 or 2, at from 70° to 180° C. optionally in the presence of further solvent and
   with the proviso that said reacting is carried out in the presence of at least the initial solvent or the further solvent or a mixture of the initial solvent and the further solvent.

2. The process as claimed in claim 1, wherein 2,2'-dimethyl-1,1'-binaphthyl and the initial solvent are used in a weight ratio of 1:(3 to 40).

3. A process as claimed in claim 1, wherein 2,2'-dimethyl-1,1'-binaphthyl and the initial solvent are used in a weight ratio of 1:(4 to 20).

4. A process as claimed in claim 1, wherein 2,2'-dimethyl-1,1'-binaphthyl and the initial solvent are used in a weight ratio of 1:(5 to 15).

5. The process as claimed in claim 1, wherein the initial solvent used is a monochlorinated or polychlorinated benzene, a monochlorinated or polychlorinated aliphatic hydrocarbon, an ester of an aliphatic carboxylic acid having from 1 to 6 carbon atoms and an aliphatic alcohol having from 1 to 4 carbon atoms or a mixture thereof.

6. The process as claimed in claim 1, wherein the initial solvent used is chlorobenzene or dichlorobenzene.

7. The process as claimed in claim 1, wherein the initial solvent used is a mixture of chlorobenzene and dichlorobenzene.

8. The process as claimed in claim 1, wherein 2,2'-dimethyl-1,1'-binaphthyl and the brominating agent are reacted under the action of light having a wavelength of from $10^{-5}$ to $10^{-8}$ m at from −10° to 75° C.

9. The process as claimed in claim 1, wherein 2,2'-dimethyl-1,1'-binaphthyl and the brominating agent are reacted under the action of light having a wave length of from $10^{-5}$ to $10^{-8}$ m at from −5 to +50° C.

10. The process as claimed in claim 1, wherein 2,2'-dimethyl-1,1'-binaphthyl and the brominating agent are reacted under the action of light having a wave length of from $10^{-5}$ to $10^{-8}$ m at from 0° to 40° C.

11. The process as claimed in claim 1, wherein 2,2'-dimethyl-1,1'-binaphthyl and the brominating agent are reacted under the action of a free-radical former at from 25 to 150° C.

12. The process as claimed in claim 1, wherein 2,2'-dimethyl-1,1'-binaphthyl and the brominating agent are reacted under the action of a free-radical former at from 40 to 135° C.

13. The process as claimed in claim 1 wherein 2,2'-dimethyl-1,1'-binaphthyl is reacted with N-bromosuccinimide as brominating agent.

14. The process as claimed in claim 1, wherein the brominating agent is N-bromosuccinimide and 2,2'-dimethyl-1,1'-binaphthyl and N-bromosuccinimide are used in a molar ratio of 1:(1.5 to 2.5).

15. The process as claimed in claim 8 wherein the brominating agent is N-bromosuccinimide which forms succinimide during bromination, and the succinimide formed is removed after bromination.

16. The process as claimed in claim 15, wherein succinimide is removed, optionally after cooling, by filtration.

17. The process as claimed in claim 15, wherein succinimide is removed by extraction with water.

18. The process as claimed in claim 15, wherein succinimide is removed in a first step by filtration and in a second step by extraction with water.

19. The process as claimed in claim 1, wherein the reaction mixture is reacted with the alkyl diphenylphosphinite of the formula RO—P(Ph—(R')$_n$)$_2$ at from 100° to 170° C.

20. The process as claimed in claim 1, wherein the reaction mixture is reacted with the alkyl diphenylphosphinite of the formula RO—P(Ph—(R')$_n$)$_2$ at from 120° to 160° C.

21. The process as claimed in claim 1, wherein the alkyl diphenylphosphinite of the formula RO—P(Ph—(R')$_n$)$_2$ is used in a molar ratio of (1.8 to 4):1 based on 2,2'-dimethyl-1,1'- binaphthyl used.

22. The process as claimed in claim 1, wherein the alkyl diphenylphosphinite of the formula RO—P(Ph—(R')$_n$)$_2$ which is used is a (C$_1$–C$_5$)-alkyl diphenylphosphinite or a mixture of (C$_1$–C$_5$)-alkyl diphenylphosphinites.

23. The process as claimed in claim 1, wherein the alkyl diphenylphosphinite of the formula RO—P(Ph—(R')$_n$)$_2$ which is used is selected from the group consisting of methyl diphenylphosphinite, ethyl diphenylphosphinite, isopropyl diphenylphosphinite, n-propyl diphenylphosphinite, ethyl bis(3-fluorophenyl)phosphinite, ethyl bis(4-fluorophenyl) phosphinite, ethyl bis(2-methylphenyl)phosphinite, ethyl bis(3-trifluoromethylphenyl) phosphinite and mixtures thereof.

24. The process as claimed in claim 1, wherein the further solvent is used which has a boiling point higher than that of the initial solvent and is added at any point during the process and wherein the initial solvent is distilled off.

25. The process as claimed in claim 24, wherein the further solvent is selected from the group consisting of o-xylene, m-xylene, p-xylene, mesitylene, and mixtures thereof, the further solvent is added during the reaction of the reaction mixture with the alkyl diphenylphosphinite and the initial solvent is selected from the group consisting of chlorobenzene, dichlorobenzene, and mixtures thereof.

26. The process as claimed in claim 1, wherein the brominating agent is N-bromosuccinimide, and wherein 2,2'-dimethyl-1,1'-binaphthyl and N-bromosuccinimide are used in a molar ratio of 1:(1.8 to 2.3).

27. The process as claimed in claim 1, wherein the brominating agent is N-bromosuccinimide and wherein 2,2'-dimethyl-1,1'-binaphthyl and N-bromosuccinimide are used in a molar ratio of 1:(1.9 to 2.2).

28. The process as claimed in claim 1, wherein the alkyl diphenylphoshinite of the formula RO—P(Ph—(R')$_n$)$_2$ is used in a molar ratio of (1.9 to 3):1 bassed on 2,2'-dimethyl-1,1'binaphthyl used.

29. The process as claimed in claim 1, wherein the alkyl diphenylphosphinite of the formula RO—P(Ph—(R')$_n$)$_2$ is used in a molar ratio of (2 to 2.5):1, based on 2,2'-dimethyl-1,1'binaphthyl used.

30. The process as claimed in claim 1, wherein the initial solvent is present in the reaction of the reaction mixture and alkyl diphenylphosphinite.

31. The process as claimed in claim 30, wherein the initial solvent is chlorobenzene, dichlorobenzene, or a mixture thereof.

* * * * *